US007341723B2

(12) United States Patent
Li et al.

(10) Patent No.: US 7,341,723 B2
(45) Date of Patent: Mar. 11, 2008

(54) NUCLEIC ACID CONSTRUCT ENCODING A PROCESSING COMPONENT DERIVED FROM THE N-TERMINAL REGION OF THE HEPATITIS VIRUS ORF2, AND AN ANTIGENIC POLYPEPTIDE

(75) Inventors: Fan Li, Bulleen (AU); David Andrew Anderson, Brunswick (AU); Damian Francis John Purcell, Balwyn North (AU)

(73) Assignee: Macfarlane Burnet Institute for Medical Research and Public Health Ltd., Melbourne (AU)

( * ) Notice: Subject to any disclaimer, the term of this patent is extended or adjusted under 35 U.S.C. 154(b) by 524 days.

(21) Appl. No.: 10/260,846

(22) Filed: Sep. 27, 2002

(65) Prior Publication Data

US 2003/0158138 A1 Aug. 21, 2003

Related U.S. Application Data

(63) Continuation of application No. PCT/AU01/00353, filed on Mar. 30, 2001.

(30) Foreign Application Priority Data

Mar. 31, 2000 (AU) .................................... PQ 6616

(51) Int. Cl.
*A61K 39/00* (2006.01)
*A61K 39/29* (2006.01)
*A61K 38/00* (2006.01)

(52) U.S. Cl. ............................... 424/184.1; 424/189.1; 530/324

(58) Field of Classification Search .............. 424/192.1
See application file for complete search history.

(56) References Cited

OTHER PUBLICATIONS

He J. et al "DNA inoculation with a plasmid vector carrying the hepatitis E virus structural protein gene induces immune response in mice" Vaccine vol. 15 (1997), No. 4, pp. 357-362.*

* cited by examiner

*Primary Examiner*—Bruce R. Campell
*Assistant Examiner*—Bo Peng
(74) *Attorney, Agent, or Firm*—Schwegman, Lundberg & Woessner P.A.

(57) ABSTRACT

A method for enhancing an immune response to a nucleic acid vaccine comprising administering to an animal a nucleic acid construct encoding a fusion protein comprising a processing component and an antigenic polypeptide of interest wherein said processing component provides heterogeneous processing of the antigenic polypeptide when the nucleic acid construct is expressed in a host cell and a resulting enhancement of the immune response. The processing component is derived from an N-terminal portion of PORF2 of Hepatitis E virus.

6 Claims, 7 Drawing Sheets

ORF2.1 series sig1 MRPRPILLLLLMFLPMLPAPPP sig2 MRPRPILLLLLMFLPMLPAPPPGQPSGRRRGRRSGG sig3 MRPRPILLLLLMFLPMLPAPPPGQPSGRRRGRRSGGSGGGFWGDRVDSQP Immunoprecipitation of labelling samples Immunoprecipitation of pulse-labelling samples Immunoprecipitation of pulse-labelling samples Western blotting against GST fusion proteins of deletion series Sig1-2.1

Sig3-2.1

SEQUENCE LISTING

<160> NUMBER OF SEQ ID NOS: 6

<210> SEQ ID NO 1
<211> LENGTH: 22
<212> TYPE: PRT
<213> ORGANISM: Hepatitis E Virus

<400> SEQUENCE: 1

```
Met Arg Pro Arg Pro Ile Leu Leu Leu Leu Leu Met Phe Leu Pro Met
 1               5                  10                  15

Leu Pro Ala Pro Pro Pro
            20
```

<210> SEQ ID NO 2
<211> LENGTH: 36
<212> TYPE: PRT
<213> ORGANISM: Hepatitis E Virus

<400> SEQUENCE: 2

```
Met Arg Pro Arg Pro Ile Leu Leu Leu Leu Leu Met Phe Leu Pro Met
 1               5                  10                  15

Leu Pro Ala Pro Pro Pro Gly Gln Pro Ser Gly Arg Arg Arg Gly Arg
            20                  25                  30

Arg Ser Gly Gly
        35
```

<210> SEQ ID NO 3
<211> LENGTH: 50
<212> TYPE: PRT
<213> ORGANISM: Hepatitis E Virus

<400> SEQUENCE: 3

```
Met Arg Pro Arg Pro Ile Leu Leu Leu Leu Leu Met Phe Leu Pro Met
 1               5                  10                  15

Leu Pro Ala Pro Pro Pro Gly Gln Pro Ser Gly Arg Arg Arg Gly Arg
            20                  25                  30

Arg Ser Gly Gly Ser Gly Gly Gly Phe Trp Gly Asp Arg Val Asp Ser
        35                  40                  45

Gln Pro
    50
```

<210> SEQ ID NO 4
<211> LENGTH: 66
<212> TYPE: DNA
<213> ORGANISM: Hepatitis E Virus

<400> SEQUENCE: 4

```
atgcgccctc ggcctatttt gctgttgctc ctcatgtttc tgcctatgct gcccgcgcca     60

ccgccc                                                                66
```

<210> SEQ ID NO 5
<211> LENGTH: 108
<212> TYPE: DNA
<213> ORGANISM: Hepatitis E Virus

<400> SEQUENCE: 5

```
atgcgccctc ggcctatttt gctgttgctc ctcatgtttc tgcctatgct gcccgcgcca     60

ccgcccggtc agccgtctgg ccgccgtcgt gggcggcgca gcggcggt                 108
```

-continued

```
<210> SEQ ID NO 6
<211> LENGTH: 150
<212> TYPE: DNA
<213> ORGANISM: Hepatitis E Virus

<400> SEQUENCE: 6

atgcgccctc ggcctatttt gctgttgctc ctcatgtttc tgcctatgct gcccgcgcca      60

ccgcccggtc agccgtctgg ccgccgtcgt gggcggcgca gcggcggttc cggcggtggt     120

ttctggggtg accgggttga ttctcagccc                                      150
```

NUCLEIC ACID CONSTRUCT ENCODING A PROCESSING COMPONENT DERIVED FROM THE N-TERMINAL REGION OF THE HEPATITIS VIRUS ORF2, AND AN ANTIGENIC POLYPEPTIDE

RELATED APPLICATIONS

This application is a continuation under 35 U.S.C. 111(a) of PCT/AU01/00353 filed Mar. 30, 2001 and published in English as WO 01/73078 A1 on Oct. 4, 2001, which claims priority from Australian application PQ 6616 filed Mar. 31, 2000, which applications and publication are incorporated herein by reference.

FIELD OF THE INVENTION

The present invention relates generally to a strategy for enhancing the immune response to nucleic acid vaccines. In particular, the present invention relates to a nucleic acid construct expressing a fusion protein comprising an antigenic polypeptide of interest and a processing peptide which enhances the antibody and/or the cellular immune response to the antigenic polypeptide of interest. The present invention is useful, inter alia, in the design and development of a wide range of methods, constructs and vectors for the modulation of the immune response to an antigen and in the diagnosis, treatment and/or prophylaxis of conditions, infections or diseases such as but not limited to cancers, autoimmune diseases or bacterial, viral or parasite infections in animals including humans and other mammals, fish and birds.

GENERAL

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word “comprise”, and variations such as “comprises” and “comprising”, will be understood to imply the inclusion of a stated integer or step or group of integers or steps but not the exclusion of any other integer or step or group of integers or steps. The present invention is not to be limited in scope by the specific embodiments described herein, which are intended for the purposes of exemplification only. Functionally-equivalent products, compositions and methods are clearly within the scope of the invention, as described herein.

Bibliographic details of the publications referred to by author in this specification are collected at the end of the description. Reference herein to prior art, including any one or more prior art documents, is not to be taken as an acknowledgment, or suggestion, that said prior art is common general knowledge or forms a part of the common general knowledge.

As used herein, the term “derived from” shall be taken to indicate that a particular integer or group of integers has originated from the species specified, but has not necessarily been obtained directly from the specified source.

This specification contains nucleotide and amino acid sequence information prepared using the program FastSeq of Windows Version 4.0, presented herein after the claims. Each sequence is identified in the sequence listing by the numeric indicator <210> followed by the sequence identifier (e.g., <210>1, <210>2, etc). The length, type of sequence (DNA, protein (PRT), etc.) and source organism for each sequence are indicated by information provided in the numeric indicator fields <211>, <212> and <213>, respectively. Nucleotide or amino acid sequences referred to in the specification are defined by the term “SEQ ID NO:”, followed by the sequence identifier (e.g., SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymidine, Y represents a pyrimidine residue, R represents a purine residue, M represents Adenine or Cytosine, K represents Guanine or Thymidine, S represents Guanine or Cytosine, W represents Adenine or Thymidine, H represents a nucleotide other than Guanine, B represents a nucleotide other than Adenine, V represents a nucleotide other than Thymidine, D represents a nucleotide other than Cytosine and N represents any nucleotide residue.

BACKGROUND OF THE INVENTION

“Nucleic acid vaccine” is a general term reflecting technologies which are used to direct the synthesis of target (vaccine) proteins in cells of the recipient, via administration of either DNA (plasmids) or self-replicating, sub-genomic viral nucleic acids (viral replicons).

Nucleic acid vaccines, and DNA vaccines in particular, in which plasmid DNAs encoding protein antigens are administered rather than the proteins themselves, have become the focus of intense research worldwide since the observation that naked DNA could induce antigen synthesis in vivo leading to the induction of immune responses (Wolff et al, 1990). Two major potential advantages in the use of nucleic acid vaccines are (a) the presentation of native epitopes to the immune system after expression of the protein in cells of the recipient, and (b) the chemical homogeneity, ease of preparation, and stability of nucleic acids, which will be of particular utility for combined vaccines and for use in the absence of the cold chain required for conventional vaccines.

The great majority of effective “traditional” vaccines are directed at acute, self-limiting infections and elicit an immune response which mimics that associated with recovery from, and immunity to, the corresponding infection. That is, they rely on the normal immune response to antigens from the infectious agent, presented in their native form(s). Nucleic acid vaccines have a strategic advantage in such systems. In the past this has generally been achieved by the use of either (i) live, attenuated vaccine organisms (e.g., Sabin polio vaccines); (ii) wild-type organisms (or bacterial toxins) which are subsequently inactivated (e.g., Salk polio vaccines), or (iii) manufacture of native antigens using recombinant DNA technology (eg subunit hepatitis B vaccines). In this context, DNA vaccines have the great advantage that the target antigens are synthesised in a native form within cells of the recipient. This is also true of viral replicon-based delivery systems (for example, the Kunjin replicon system (Khromykh, et al. 1997; Varnavski, et al.

1999; Varnavski, et al. 2000). However, antibody responses to DNA vaccines encoded antigens are frequently low or undetectable.

Much less progress has been made in the development of preventative and therapeutic vaccines against infections where the normal immune response fails to clear the infection. For agents such as HCV and the Human Immunodeficiency Virus (HIV) where failure to clear infection is the norm, vaccines which are able to induce the normal immune response to relevant antigens may have little utility. This is also true of tumour-specific antigens which are usually seen as "self" and thus the normal immune response is one of tolerance. Despite their many potential advantages, standard DNA or replicon vaccines may be ineffective in such cases, precisely because they encode antigens in their native forms.

A variety of methods have been used to modulate immune responses to DNA vaccines, including (i) co-delivery of cytokines or cytokine-encoding plasmids; (ii) the immunostimulatory role of CpG dinucleotides commonly found in bacterial (and plasmid) DNAs (Hemmi et al, 2000); and (iii) prime-boost protocols, utilising DNA vaccines together with poxvirus vectors.

Existing strategies for antigen targeting include the use of (a) ubiquitin fusions (ubiquitin-A76 or -G76-K) to target proteins for polyubiquitination, rapid intracellular degradation in proteasomes and efficient MHC-I presentation; (b) fusion to lysosome-associated membrane protein 1 (LAMP-1) to target the MHC-II pathway; (c) fusion to the adenovirus E3 leader sequence to target the epitope to the endoplasmic reticulum (ER); and (d) fusion to CTLA4 to target the epitope for secretion and uptake by professional antigen presenting cells (APCs).

However, the efficacy of many DNA vaccines has been poor (Gurunathan S et al, 2000) and there is a need for the development of improved technologies and molecules to modulate the immune response to proteins expressed by DNA vaccines leading to recovery or protection.

SUMMARY OF THE INVENTION

In the work leading up to the present invention, the inventors have shown that when the full-length capsid protein, PORF2, of Hepatitis E Virus (HEV) is expressed in mammalian cells, approximately 80% of the newly synthesised protein is translocated to the endoplasmic reticulum and rapidly degraded while 20% of protein accumulates in an intact form within the cytosol (4).

In accordance with the present invention, the inventors have identified N-terminal peptide sequences of the PORF2 of HEV that permit heterogeneous polypeptide processing ("processing peptide" or "processing component") and have also developed a strategy for enhancing the immune response to an antigenic polypeptide of interest using such processing peptide sequences.

The inventors expressed the PORF2.1 antigenic polypeptide fragment of HEV in animal cells using a series of expression vectors encoding the ORF2.1 fragment without a fusion protein (ORF2.1) or as fusion proteins with sequences from the N-terminus of PORF2 of HEV; Sig1-ORF2.1 having amino acids 1 to 22 of PORF2, Sig2-ORF2.1 having amino acids 1 to 36 of PORF2 or Sig3-ORF2.1 having amino acids 1 to 50 of PORF2. The inventors established that while ORF2.1 protein was found almost exclusively in the soluble cytosol fraction, the Sig1 peptide is directed almost exclusively to the membrane fraction while Sig 2 and Sig 3 peptides confer a heterogeneous localisation. Furthermore, in the case of the Sig2-ORF2.1 and Sig3-ORF2.1 polypeptides, the cytosol-associated protein was found to be stable while the membrane-associated protein was degraded consistent with the generation of a mixed immune response (antibody and CTL responses respectively).

The broad generality of this finding was confirmed when the N-terminal sequences of ORF2 (Sig1, Sig2 and Sig3) were fused to Glutathione-S-transferase and shown to be processed (i.e., localised and processed) heterogeneously in the same way.

The ability of the processing peptides to enhance an immune response to an antigenic polypeptide compared to the unmodified protein was tested in a rat model in which an antibody response to PORF2.1 was measurable. Sig1-ORF2.1 and Sig3-ORF-2.1 induced an enhanced antibody response and in the case of Sig3-ORF2.1 most of the translocated fraction was degraded rapidly which favours MHC-I pathway presentation and the induction of cellular immune responses.

Accordingly, one aspect of the present invention provides a method for enhancing, in an animal, an immune response to an antigenic polypeptide of interest, said method comprising administering to said animal an effective amount of a composition comprising a nucleic acid construct encoding a fusion protein comprising a processing component and said antigenic polypeptide wherein said processing component provides heterogeneous processing of the antigenic polypeptide when the nucleic acid construct is expressed in a host cell and a resulting enhancement of the immune response to the antigenic polypeptide.

Another aspect of the present invention provides an isolated nucleic acid molecule comprising a sequence of nucleotides encoding a processing peptide capable of modulating the immune response to an antigenic polypeptide in a host when said nucleic acid molecule is expressed in a host cell as a fusion protein comprising the processing peptide and the antigenic polypeptide.

In another aspect, the present invention provides an isolated nucleic acid molecule comprising a sequence of nucleotides encoding a processing peptide providing heterogeneous processing of an antigenic polypeptide of interest when said nucleic acid molecule is expressed in a host cell as a fusion protein comprising the processing peptide and the antigenic polypeptide.

Another aspect of the present invention provides an isolated nucleic acid molecule encoding a processing peptide capable of enhancing the immune response to an antigenic polypeptide in a host when said nucleic acid molecule is expressed in a host cell as a fusion protein comprising the processing peptide and the antigenic polypeptide wherein said processing peptide is encoded by a sequence of contiguous nucleotides of the N-terminal region of the ORF2 nucleotide sequence of Hepatitis E Virus or a functional derivative, variant, part or homologue thereof.

Still another aspect of the present invention provides an isolated nucleic acid molecule encoding a processing peptide capable of modulating the immune response to an antigenic polypeptide in a host when said nucleic acid molecule is expressed in a host cell as a fusion protein comprising the processing peptide and the antigenic polypeptide wherein said processing peptide comprising a sequence of about 5-100 contiguous amino acids selected from the N-terminal region of the PORF2 protein of Hepatitis E Virus or a functional derivative, variant, part or homologue thereof.

In one embodiment of the present invention the isolated nucleic acid molecule comprises a sequence of nucleotides substantially as set forth in SEQ ID NO: 4 or SEQ ID NO: 5 or SEQ ID NO: 6 or a functional derivative, variant, part or homologue thereof.

Still another aspect of the present invention provides an isolated polypeptide comprising a sequence of amino acids of about 5-100 contiguous amino acids selected from the N-terminal region of the PORF2 protein of Hepatitis E Virus or functional derivative, variant, part or homologue thereof.

Preferably, the isolated polypeptide as hereinbefore described has an amino acid sequence substantially as set forth in SEQ ID NO: 1 or SEQ ID NO: 2 or SEQ ID NO: 3 or a functional derivative, variant, part or homologue thereof.

A further aspect of the present invention provides a nucleic acid construct comprising a sequence of nucleotides encoding a fusion protein wherein said fusion protein comprises a processing component and at least one antigenic component, wherein said processing component provides for heterologous processing of the antigenic component and a resulting enhancement of the immune response to said antigenic component in a host when the nucleic acid construct is expressed in a host cell.

Another related aspect of the present invention provides a nucleic acid construct comprising a sequence of nucleotides encoding a fusion protein, said fusion protein comprising a processing component and at least one antigenic component in a host, said processing component being capable of enhancing the immune response to said antigenic component, and comprising a signal sequence and optionally an intermediate peptide comprising a sequence of amino acids substantially corresponding to the N-terminal region of a protein which is capable of heterogeneous intracellular processing.

Preferably, the processing component as hereinbefore described comprises both a signal sequence and an intermediate peptide comprising a sequence of amino acids substantially corresponding to the N-terminal region of a protein which is capable of heterogeneous intracellular processing.

Yet another aspect of the present invention provides a nucleic acid construct comprising a sequence of nucleotides encoding a fusion protein, said fusion protein comprising a processing component and at least one antigenic component, said processing component being capable of enhancing the immune response to said antigenic component, said processing component comprising a signal sequence and optionally an intermediate peptide comprising a sequence of amino acids substantially corresponding to the N-terminal region of the major structural protein of Hepatitis E Virus (PORF2) or a functional derivative, variant, part or homologue thereof.

Preferably, the processing component as hereinbefore described comprises both a signal sequence and an intermediate peptide sequence from the N-terminal region of the major structural protein of Hepatitis E Virus (PORF2) or a functional derivative, variant, part or homologue thereof.

Still yet another aspect of the present invention provides a nucleic acid construct comprising a sequence of nucleotides encoding a fusion protein wherein said fusion protein comprises a processing component and at least one antigenic component, said processing component being capable of modulating the immune response to said antigenic component in a host, and comprising a sequence of amino acids of about 5 to 100 contiguous amino acids selected from the N-terminal region of the major structural protein of Hepatitis E Virus (PORF2) or a functional derivative, variant, part or homologue thereof.

In a particularly preferred aspect of the present invention, the processing component of the fusion protein comprises a sequence of amino acids substantially as set forth in SEQ ID NO: 1 or SEQ ID NO: 2 or SEQ ID NO: 3 corresponding to amino acids 1-22, 1-36 or 1-50 respectively of the N-terminal region of PORF2 or a functional derivative, variant, part or homologue thereof.

A still further aspect of the present invention provides an isolated nucleic acid construct comprising a sequence of nucleotides encoding a fusion protein, wherein said fusion protein comprises a processing component encoded by an 5' region of ORF2 gene of Hepatitis E Virus and an antigenic component, wherein said processing component modulates the immune response to the antigenic component in a host when the nucleic acid construct is expressed in a host cell.

Yet a further aspect of the present invention provides a vaccine comprising a nucleic acid construct as hereinbefore described, such as, for example, a viral replicon or DNA molecule, A related aspect of the invention provides a cell, such as, for example, an antigen presenting cell, transfected with a nucleic acid construct as hereinbefore described.

Still yet another aspect of the present invention provides a composition for use in enhancing the immune response in an animal comprising a nucleic acid construct as hereinbefore described and one or more pharmaceutically acceptable carriers and/or diluents.

Even still yet another aspect of the present invention provides a method for modulating, in a animal, an immune response to an antigen of interest, said method comprising administering to said animal an effective amount of a nucleic acid construct as hereinbefore described, or vaccine or cell encoding or comprising a nucleic acid construct as hereinbefore described, for a time and under conditions sufficient to modulate the immune response to said antigen.

The present invention also extends to the use of a nucleic acid molecule or construct as hereinbefore described in the manufacture of a medicament for the treatment or prophylaxis of conditions or infections including but not limited to cancer or pre-cancerous conditions, autoimmune diseases, viral, bacterial or parasitic infections in animals including humans and other mammals, fish or birds.

Abbreviations: Ab, linear: antibody to linear peptide epitopes. Ab, conform.: antibody to conformational peptide epitopes. CTL: cellular immune responses.

Figure 6:
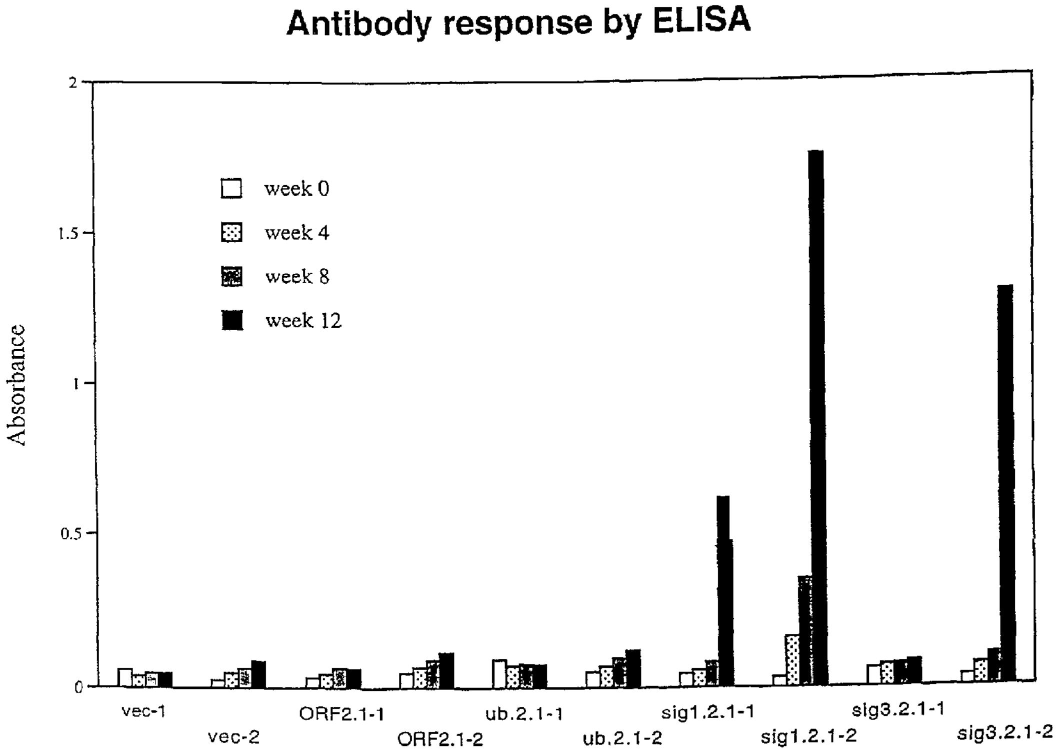

FIG. 6 is a graphical representation showing the development of antibody to HEV ORF2.1 in rats immunised with various DNA vaccine constructs (vec; vector alone; ORF2.1 alone, Ub.2.1; ubiquitin-A76-ORF2.1, sig1.2.1; Sig1-ORF2.1, sig3.2.1; Sig3-ORF2.1). Two rats per group were immunised via IM injection of 100 μg DNA in saline at 0, 4 and 8 weeks, and antibody responses at the indicated times were measured using the ORF2.1 ELISA (Anderson et al, 1999).

Figure 7:
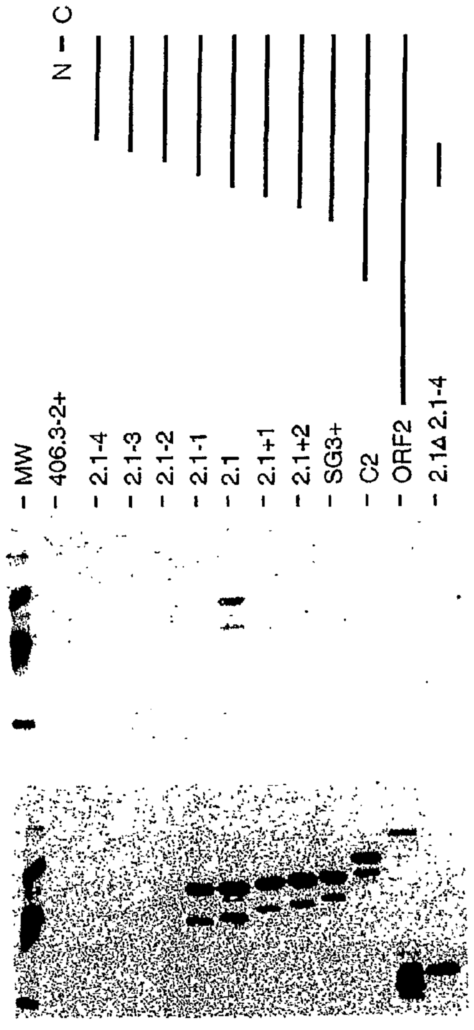

FIG. 7 is a representation is a Western blot showing development of antibody to HEV ORF2.1 in rats immunised with DNA vaccine constructs. Antibody from rats immunised with Sig1-ORF2.1 or Sig3-ORF2.1 were tested by Western Immunoblotting against various fragments of the full-length ORF2 protein as described in Riddel et al (2000). Note that the Sig1-ORF2.1 DNA vaccine induces antibody to the conformational ORF2.1 epitope, while the Sig3-ORF2.1 DNA vaccine induces a high level of antibody against both the conformational ORF2.1 epitope as well as linear epitopes, consistent with presentation of both intact and degraded antigen through the MHC-II pathway.

TABLE 1

SUMMARY OF SEQ ID NOS

| SEQUENCE | SEQ ID NO: |
|---|---|
| amino acid sequence Sig1 of PORF2 of HEV | 1 |
| amino acid sequence Sig2 of PORF2 of HEV | 2 |
| amino acid sequence Sig3 of PORF2 of HEV | 3 |
| nucleic acid sequence of Sig1 of ORF2 of HEV | 4 |
| nucleic acid sequence of Sig2 of ORF2 of HEV | 5 |
| nucleic acid sequence of Sig3 of ORF2 of HEV | 6 |

DETAILED DESCRIPTION OF PREFERRED EMBODIMENTS

The present invention is predicated in part on the identification of N-terminal peptides of the PORF2 capsid protein of Hepatitis E Virus which confer unique patterns of intracellular protein processing to fusion proteins comprising one of these peptides fused to heterologous proteins. Methods for generating suitable expression vectors and cloning strategies are well known in the art. In this way, DNA vaccine-encoded antigen can be simultaneously processed for optimal stimulation of both the cellular and humoral immune responses.

It is envisaged that nucleic acid constructs encoding the processing peptide sequences of the present invention fused to any antigenic peptide or polypeptide of interest will modulate the immune response to the polypeptide of interest when the nucleic acid construct is expressed in a host cell.

Recent research on nucleic acid vaccines has shown that cellular immune responses are enhanced by rapid degradation of protein through the proteasome pathway, achieved by fusion to ubiquitin, whereas such degradation largely abrogates antibody (humoral) immune responses to the same proteins (8 and 9). Similarly, different immune responses are elicited by expression of the same antigenic protein targeted to remain cell-associated or excreted from the cell (3). The cellular and humoral immune responses to nucleic acid vaccines are therefore sensitive to the pattern of intracellular protein processing of the antigen. In many cases, both arms of the immune pathway may be required for protective efficacy of vaccines, and a balanced response may require differential processing of a particular antigenic protein.

When protein antigens are expressed in the cell, their intracellular processing is generally homogeneous. That is, every copy of the protein will be processed in essentially the same way, for example by translocation to the endoplasmic reticulum and subsequent cell surface expression or excretion, or alternatively by retention in the cytosol or targeting for degradation in the proteasome or other degradative pathways. As a result, the expression of a protein after administration of a nucleic acid vaccine will result in a homogeneous pattern of processing for the encoded protein, biasing the immune response towards cellular or humoral pathways depending on the processing pathway for that particular protein.

For many diseases, it is not known whether humoral or cellular immunity is more likely to provide protection from disease or therapeutic effects, and it is likely that both arms of the immune response will often be required for optimal protection or therapeutic effects. In addition, there are many diseases which are characterised by the lack of a protective or therapeutic immune response in affected individuals, such as cancers and infections with chronic viruses such as hepatitis C, hepatitis B and the human immunodeficiency viruses (HIV-1 and HIV-2). For these diseases, it is clear that the normal pattern of protein processing for the protein antigens associated with the disease does not elicit an immune response which can lead to recovery or protection.

Accordingly, one aspect of the present invention provides a method for enhancing, in an animal, an immune response to an antigenic polypeptide of interest, said method comprising administering to said animal an effective amount of a composition comprising a nucleic acid construct encoding a fusion protein comprising a processing component and said antigenic polypeptide wherein said processing component provides heterogeneous processing of the antigenic polypeptide when the nucleic acid construct is expressed in a host cell and a resulting enhancement of the immune response to the antigenic polypeptide.

In one embodiment, said nucleic acid construct encoding a processing component encodes a processing component comprising a sequence of amino acids as set forth in SEQ ID NO: 2 or SEQ ID NO: 3 or a functional derivative, variant, part or homologue thereof.

Reference herein to "enhancing the immune response" or "modulating the immune response" should be understood as including reference to up-regulating and down-regulating one or more arms of the immune response and includes optimal stimulation of the cellular and/or the humoral (antibody) immune response and may also include advantageous feedback mechanisms between these two arms of the immune response. Activation of humoral immune responses in addition to cellular immune responses may also have an added advantage of modulating inflammatory responses and in particular $T_H$1-type immune cells. According to a preferred embodiment, heterogeneous processing of antigenic polypeptides permits enhanced mixed immune responses ie, both antibody and cellular responses.

Reference herein to a "processing component" or "processing peptide" of a fusion protein should be understood as including reference to a peptide or polypeptide which affects inter alia the intracellular localisation and/or proteolytic processing of the fusion protein. Preferably, the processing component enables heterogeneous intracellular localisation of the antigenic component. The processing component may be from HEV or it may be from any other source. The processing peptide may be positioned 5' to the antigenic polypeptide. Alternatively the processing polypeptide may function from a 3' position relative to the antigenic polypeptide. As a further alternative, the processing component may function from a nested position within the fusion protein. Clearly, the fusion proteins contemplated by the present inventors do not extend to naturally occurring molecules. Those skilled in the art will appreciate that the methods described herein may be used to identify further processing peptides that permit heterogeneous processing of fusion proteins containing them.

Another aspect of the present invention provides an isolated nucleic acid molecule comprising a sequence of nucleotides encoding a processing peptide capable of modulating the immune response to an antigenic polypeptide in a host when said nucleic acid molecule is expressed in a host cell as a fusion protein comprising the processing peptide and the antigenic polypeptide.

Still another aspect of the present invention provides an isolated nucleic acid molecule as hereinbefore described comprising a sequence of nucleotides substantially corresponding to the N-terminal region of the ORF2 gene of Hepatitis E Virus or a functional derivative, variant, part or homologue thereof.

Still another aspect of the present invention provides an isolated nucleic acid molecule as hereinbefore described encoding a processing peptide comprising a sequence of about 5-100 contiguous amino acids selected from the N-terminal region of the PORF2 protein of Hepatitis E Virus or a functional derivative, variant, part or homologue thereof.

According to this particular aspect of the invention amino acid 1 is the most N-terminal amino acid. The N-terminal region may comprise up to about 100 amino acids.

Preferably, the subject peptide comprises amino acids 1-22 or 1-36 of the N-terminal region of PORF2, even more preferably the subject peptide comprises amino acids 1-50 of the N-terminal region of PORF2 or a functional derivative, variant, part or homologue thereof.

Reference to "functional" according to this aspect of the invention includes reference to polypeptides and their encoding polynucleotides which are capable of modulating the immune response when the polynucleotide is expressed in a host cell.

One aspect of the present invention provides a nucleic acid construct comprising a sequence of nucleotides encoding a fusion protein, wherein said fusion protein comprises a processing component and at least one antigenic component, said processing component being located 5' to the antigenic component and being capable of enhancing the immune response to said antigenic component in a host when said nucleic acid construct is expressed in a host cell.

The nucleic acid molecule suitable for use in the present invention may be any form of nucleic acid molecule such as DNA or RNA.

In one particular embodiment of this aspect of the invention, the processing component comprises a signal sequence which directs the fusion protein to a membrane and cytosol localisation in a host cell where the fusion protein is stable over a period of hours and is effective in enhancing an antibody response to the antigenic component.

In a preferred aspect of the invention, the processing component confers the properties of heterogeneous intracellular localisation (ie. to cytosol and membrane compartments) and/or mixed intracellular proteolytic processing (stable and degraded). Without limiting the present invention to any one mode or theory of action, it is thought that the processing component of the present invention simultaneously targets the fusion protein for optimal stimulation of both the cellular and humoral immune responses.

Accordingly, another aspect of the present invention provides an nucleic acid construct comprising a sequence of nucleotides encoding a fusion protein wherein said fusion protein comprises a processing component and at least one antigenic component, said processing component being located 5' to the antigenic component and being capable of modulating the immune response to said antigenic component in a host, said processing component comprising a signal sequence and optionally an intermediate peptide comprising a sequence of amino acids substantially corresponding to the N-terminal region of a protein which is capable of heterogeneous intracellular post-translational processing.

Preferably, the processing component as hereinbefore described comprises both a signal sequence and an intermediate peptide comprising a sequence of amino acids substantially corresponding to the N-terminal region of a protein which is capable of heterogeneous intracellular post-translational processing.

Reference herein to a "signal sequence" should be understood as including reference to a peptide usually, but not necessarily, located at the N-terminus of a newly synthesised polypeptide. The signal sequence may direct post-translational uptake by organelles and may be cleaved off as the protein matures. It includes any eukaryotic or prokaryotic signal sequence which may be associated, in its naturally occurring form, with the antigenic protein of interest or from any other useful source. In accordance with the present invention, the signal sequence may be fully functional and fully cleaved or alternatively cleavage and/or signal sequence function may be inefficient. As known to those skilled in the art, the signal sequence of a polypeptide may be predicted using various known algorithms (G. von Heijne et al, 1989).

Yet another aspect of the present invention provides a nucleic acid construct comprising a sequence of nucleotides encoding a fusion protein wherein said fusion protein comprises a processing component and at least one antigenic component in a host, said processing component being located 5' to the antigenic component and being capable of modulating the immune response to said antigenic component, said processing component comprising a signal sequence and optionally an intermediate peptide comprising a sequence of amino acids substantially corresponding to the N-terminal region of the major structural protein of Hepatitis E Virus (PORF2) or a functional derivative, variant, part or homologue thereof.

Preferably, the processing component as hereinbefore described comprises both a signal sequence and an intermediate peptide comprising a sequence of amino acids substantially corresponding to the N-terminal region of the major structural protein of Hepatitis E Virus (PORF2) or a functional derivative, variant, part or homologue thereof.

Reference herein to an “intermediate peptide sequence” should be understood as including reference to sequences positioned 3' of the signal sequence, which 3' sequences alter the processing properties conferred by the processing component on the fusion protein. As with the signal sequence, the intermediate peptide sequence may originate from any source including the N-terminal region of PORF2 of Hepatitis E Virus.

Still yet another aspect of the present invention provides a nucleic acid construct comprising a sequence of nucleotides encoding a fusion protein wherein said fusion protein comprises a processing component and at least one antigenic component, said processing component being located 5' to the antigenic component and being capable of modulating the immune response to said antigenic component, said processing component comprising a signal sequence and an intermediate peptide wherein said processing component comprises a sequence of amino acids substantially corresponding to 5 to 100 contiguous amino acids selected from the N-terminal region of the major structural protein of Hepatitis E Virus (PORF2) or a functional derivative, variant, part or homologue thereof.

In one embodiment, the processing component comprises approximately 5-100 amino acids, more preferably 30-90 and even more preferably 20-60 amino acids selected from the N-terminal region of PORF2 or a functional derivative, variant, part or homologue thereof.

Preferably, the processing component comprises a sequence of amino acids substantially as set forth in SEQ ID NO: 1 or SEQ ID NO: 2 or SEQ ID NO: 3 corresponding to amino acids 1-22, 1-36 or 1-50 respectively of the N-terminal region of PORF2 protein or a functional derivative, variant, part or homologue thereof.

Reference to “derivatives” according to this aspect of the present invention, includes fragments, parts, portions, equivalents, analogues, mutants, mimetics or homologues. Polypeptide derivatives may be derived by insertion, deletion or substitution of the amino acids. Polynucleotide derivatives may be derived from single or multiple nucleic acid substitutions, deletions, and/or additions including fusion with other nucleic acid molecules. Equivalents are understood to include reference to molecules which can act as functional analogues or agonists. Equivalents may be detected following, for example, natural product screening. Reference to “variants” includes reference to molecules having at least 50% or preferably 60% or between 65-80% similarity and most preferably at least 90% similarity to the polypeptide or polynucleotide sequence. Functional variants may be established by mutagenesis studies or through rational design. Furthermore, polynucleotide variants may also include polynucleotides capable of hybridising to the polynucleotides of the present invention under conditions of medium stringency.

In a related aspect of the present invention, the processing component of the fusion protein comprises a peptide encoded by a sequence of 1-300 nucleotides substantially corresponding to contiguous nucleotides of the N-terminal region of the ORF2 gene of HEV.

Preferably, the processing component comprises a peptide encoded by a sequence of nucleotides substantially as set forth in SEQ ID NO: 4 or SEQ ID NO: 5 or SEQ ID NO: 6 or functional derivative, variant, part or homologue thereof.

A further aspect of the present invention provides an nucleic acid construct comprising a sequence of nucleotides encoding a fusion protein, wherein said fusion protein comprises a processing component encoded by a 5' region of ORF2 of Hepatitis E Virus and an antigenic component, wherein said processing component modulates the immune response to the antigenic component in a host when the nucleic acid construct is expressed in a host cell.

Yet a further aspect of the present invention provides a vaccine comprising a nucleic acid construct as hereinbefore described.

A further related aspect of the invention provides a cell transfected with a nucleic acid construct as hereinbefore described. A suitable cell for use in the present invention may be an immune cell and/or a presentation cell capable of presenting or targeting or directing the fusion protein within a host organism so as to optimise the immune response to the antigenic component. According to this aspect, the cell may be transfected in vitro or in vivo. One particularly preferred cell type is a dendritic cell.

Still yet another aspect of the present invention provides a composition for use in modulating the immune response in a animal comprising a nucleic acid construct as hereinbefore described and one or more pharmaceutically acceptable carriers and/or diluents.

Reference herein to “animal” is used in a broad sense to include mammals, birds, fish and reptiles, and extends to animals such as but not limited to a human, primate, livestock animal (eg. sheep, pig, cow, horse) companion animal (eg dog, cat), laboratory test animal (eg. mouse, rat, rabbit, guinea pig, hamster), captive wild animal (eg. fox, deer), caged bird (eg. parrot) and poultry bird (eg. chicken, duck) Preferably, the subject animal is a human or primate. Most preferably, the subject is a human.

The pharmaceutical forms suitable for injectable use include sterile aqueous solutions (where water soluble) and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of surfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying or promoting agents and the like. The use of such media and agents for pharmaceutical active substances is well known in the art. Except insofar as any conventional media or agent is incompatible with the active ingredient or cell, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 μg to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients.

Administration of the nucleic acid construct or vaccine in the form of a composition may be by any convenient mode such as, but not limited to, direct administration by gene gun, liposome or polymeric microsphere delivery or delivery via viral based vectors. The agent of the pharmaceutical composition is contemplated to exhibit therapeutic or prophylactic activity in an amount which depends on the particular case. The variation depends upon, for example, on the animal, the mode of administration and the treatment required. A broad range of doses may be applicable. Considering a patient, for example, from about 0.1 μg to about 1 mg of nucleic acid construct may be administered per kilogram of body weight. Dosage regimes may be adjusted to provide the optimum therapeutic response. The agent may be administered in any convenient manner such as by the oral, intravenous (where water soluble), intranasal, intraperitoneal, intramuscular, subcutaneous, intradermal or suppository routes or implanting (e.g. using slow release molecules).

Even still yet another aspect of the present invention provides a method for modulating, in a animal, an immune response to an antigen of interest said method comprising administering to said animal an effective amount of a nucleic acid construct as hereinbefore described, or vaccine or cell encoding or comprising a nucleic acid construct as hereinbefore described, for a time and under conditions sufficient to modulate the immune response to said antigen.

The above method may provide a particularly useful method for antibody production including monoclonal antibody production in a laboratory animal or in vitro or in vivo.

The present invention also extends to the use of a nucleic acid construct as hereinbefore described in the manufacture of a medicament for the treatment or prophylaxis of conditions or infections including but not limited to, cancer or pre-cancerous conditions, autoimmune diseases, viral, bacterial or parasitic infections.

Further features of the present invention are more fully described in the following non-limiting Examples.

EXAMPLE 1

Figure 1:
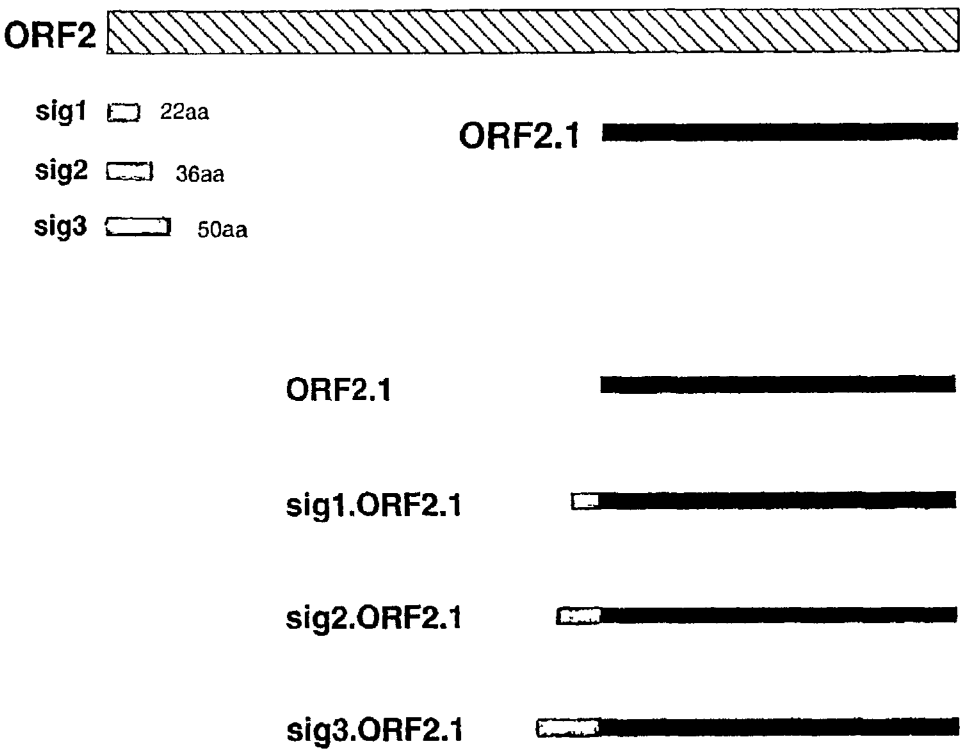
FIG. 1 provides a map of the sig1, sig2 and sig3 (SEQ ID NOs: 1-3) peptides relative to the full-length PORF2 protein of Hepatitis E Virus, and the amino acid sequences of the respective proteins. It is apparent that proteins of intermediate size between these examples would be expected to have similar utility.

Differential Localisation of HEV Fusion Proteins to Cytosolic or Membrane Associated Fractions of Cells The HEV-encoded antigenic protein ORF2.1 was expressed in mammalian cells using a series of expression vectors which encode ORF2.1 without a fusion protein (ORF2.1) or with N-terminal fusion proteins of sig1 (sig1-2.1), sig2 (sig2-2.1) or sig3 (sig3-2.1) (FIG. 1). Cells were incubated in the presence of radioactive methionine and cysteine to label newly synthesised proteins, cells were fractionated into the soluble cytosolic (c) and membrane fractions (m), and proteins containing ORF2.1 sequences were selected by immunoprecipitation with specific ORF2.1 polyclonal antibodies and were detected by SDS-PAGE and autoradiography. It can be seen that while ORF2.1 is almost exclusively found in the soluble cytosol fraction, sig1-2.1 is found almost exclusively in the membrane fraction while sig2-2.1 and sig3-2.1 are found in similar proportions in both fractions. Note that the multiple bands of different migration rates are due to partial glycosylation of those proteins which are translocated to the membrane fraction, as they are abolished when cells are treated with tunicamycin to prevent N-glycosylation (not shown). This figure demonstrates the unique effects which each sig protein confers to protein localisation within the cell, especially with respect to sig2 and sig3 conferring a heterogeneous localisation.

EXAMPLE 2

Differential Stability of HEV Fusion Proteins

Figure 2:
FIG. 2 is a representation of immunoprecipitation and PAGE of radioactively labelled ORF2.1 and sig1-2.1, sig2-2.1 and sig3-2.1 showing the differential localisation of encoded proteins into the cytosolic (c) or membrane-associated (m) fractions of the cells. Note that ORF2.1 and sig1-2.1 have homogeneous localisation, whereas sig2-2.1 and sig3-2.1 have heterogeneous localisation. Note also that the multiple bands of different migration rates are due to partial glycosylation of those proteins which are translocated to the membrane fraction.
Figure 3:
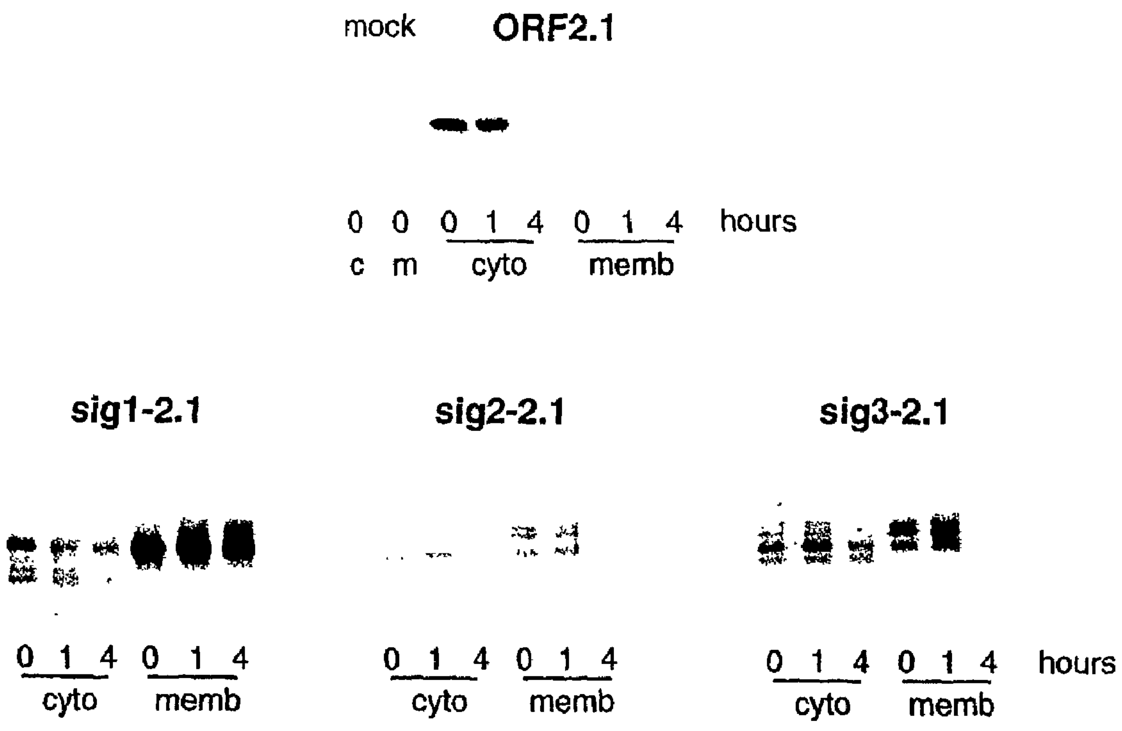
FIG. 3 is a representation of immunoprecipitation and PAGE analysis of radioactively labelled ORF2.1 and sig1-2.1, sig2-2.1 and sig3-2.1 showing the differential localisation of encoded proteins into the cytosolic (cyto) or membrane-associated (memb) fractions of the cells (as for FIG. 2), and the differential stability of each protein species at 0, 1 or 4 hours after labelling. Note that ORF2.1 and sig1-2.1 have homogeneous processing (degraded or stable after 4 h, respectively), whereas sig2-2.1 and sig3-2.1 have heterogeneous processing (stable and degraded) consistent with their heterogeneous localisation (cyto and memb, respectively).
Figure 4:
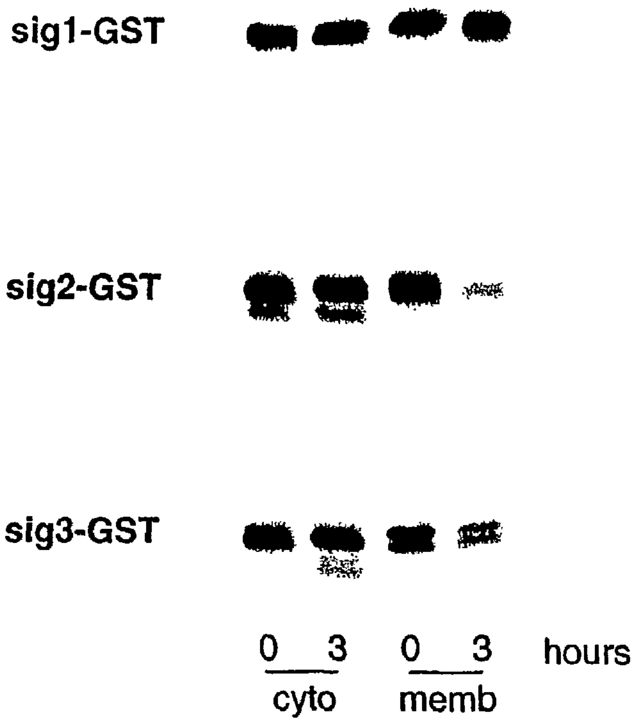
FIG. 4 is a representation of immunoprecipitation and PAGE analysis of radioactively labelled sig1-GST, sig2-GST and sig3-GST showing the differential localisation of encoded proteins into the cytosolic (cyto) or membrane-associated (memb) fractions of the cells and the differential stability of each protein species at 0 or 3 hours after labelling. Note that sig1-GST has heterogeneous localisation (cyto plus memb) but homogeneous processing (stable), whereas sig2-GST and sig3-GST have heterogeneous localisation (cyto plus memb) and heterogeneous processing (stable and degraded).

Cells expressing each protein were incubated in the presence of radioactive amino acids as in FIG. 2, but were then further incubated in the presence of an excess of non-radioactive amino acids for various times before fractionation and analysis as before. This allows us to define the processing pattern for each of the proteins, by comparing the amount of each radioactive protein at the end of radioactive labelling (time 0 hours) versus 1 or 4 hours of further incubation in the cell. It can be seen (FIG. 3) that the protein ORF2.1 is found predominantly in the cytosol (cyto) and is stable 1 hour after synthesis, whereas protein sig1-2.1 is found predominantly in the membrane fraction (memb) and is stable at 4 hours after synthesis. In contrast, sig2-2.1 and sig3-2.1 are each found in both cyto and memb fractions, with the cyto-associated protein being stable after 4 hours while the memb-associated protein is almost completely degraded after 4 hours. It is therefore expected that sig2-2.1 and sig3-2.1 in these examples would give rise to mixed immune responses to the ORF2.1 protein due to their heterogeneous processing and localisation, whereas ORF2.1 and sig1-2.1 would each give a single pattern of immune response due to their homogenous processing and localisation.

EXAMPLE 3

Differential Localisation and Stability of SIG.GST Fusion Proteins

Sig1, sig 2 or sig3 were fused to glutathione S-transferase (GST) for expression in mammalian cells as in Example 2. In this example, it can be seen that sig1-GST has a heterogeneous localisation with equal proportions in the cyto and memb fraction, but homogeneous processing with both fractions being stable after 4 h. In contrast, sig2-GST and sig3-GST have heterogeneous localisation with equal proportions in the cyto and memb, fractions at 0 hours, and also heterogeneous processing with the cyto fraction being stable after 3 h while the memb fraction is almost completely degraded after 3 h. It is therefore expected that the use of these sig1, sig2 or sig3 fusion proteins would modulate immune responses to target antigens with GST as the example.

EXAMPLE 4

Nucleic Acid Sequence of Sig1, Sig2 and Sig3

The following sequences were derived by PCR amplification of appropriate fragments from the full length ORF2 sequence with addition of restriction sites in the primers.

```
Sig1 SEQ ID NO: 4
ATGCGCCCTCGGCCTATTTTGCTGTTGCTCCTCATGTTTCTGCCTATGCT
GCCCGCGCCACCGCCC

Sig2 SEQ ID NO: 5
ATGCGCCCTCGGCCTATTTTGCTGTTGCTCCTCATGTTTCTGCCTATGCT
GCCCGCGCCACCGCCCGGTCAGCCGTCTGGCCGCCGTCGTGGGCGGCGCA
GCGGCGGT

Sig3 SEQ ID NO: 6
ATGCGCCCTCGGCCTATTTTGCTGTTGCTCCTCATGTTTCTGCCTATGCT
GCCCGCGCCACCGCCCGGTCAGCCGTCTGGCCGCCGTCGTGGGCGGCGCA
GCGGCGGTTCCGGCGGTGGTTTCTGGGGTGACCGGGTTGATTCTCAGCCC
```

The mammalian expression vector used for expression was pCl-neo (Promega) which has the CMV immediate early promoter, SV40 polyadenylation and chimeric splice signal.

EXAMPLE 5

Immunisation of Balb/C Mice with Plasmid Constructs

Figure 5:
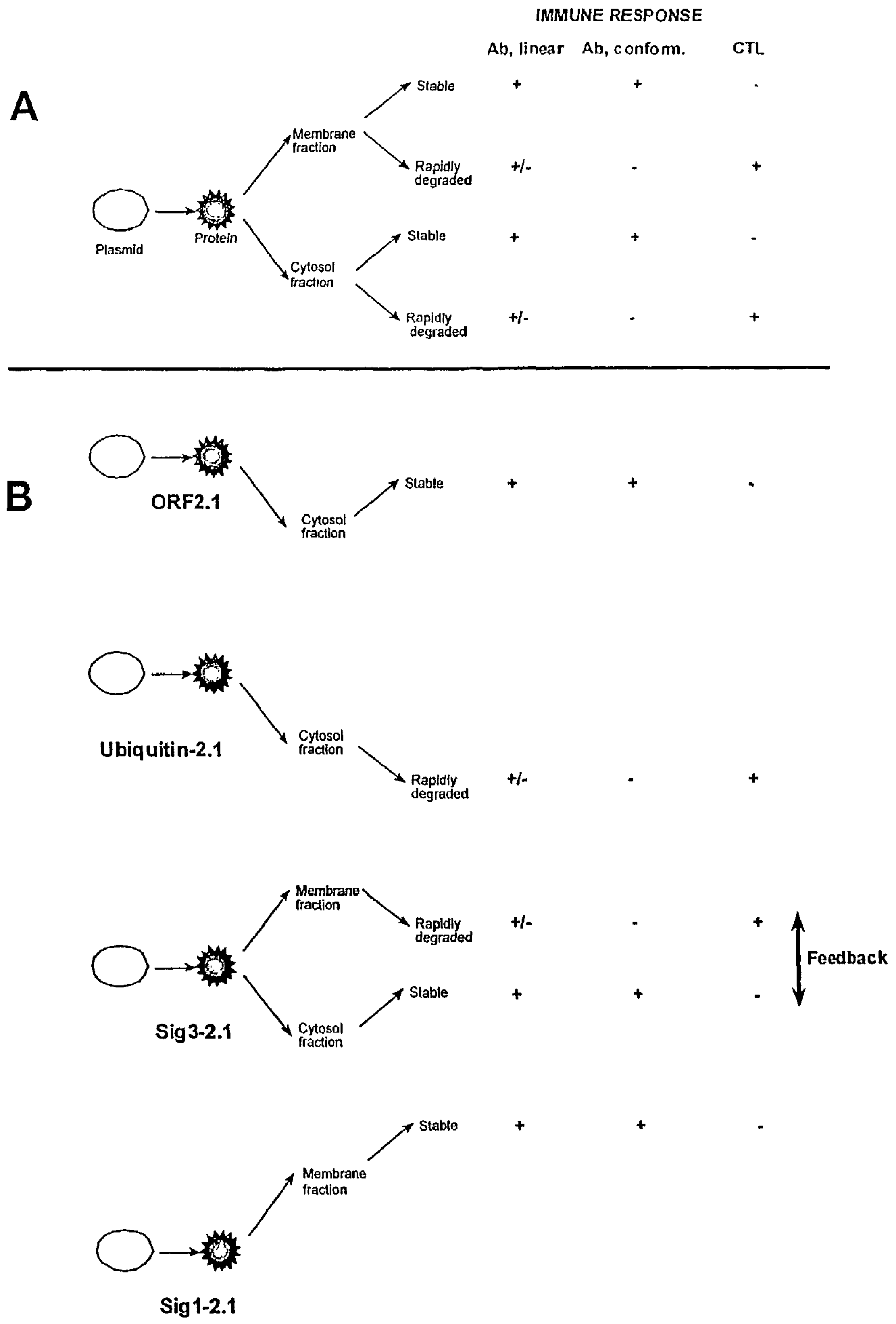
FIG. 5 is a diagrammatic representation of the immune responses to nucleic acid or viral vector-based vaccines in animals or man. (A). General pattern of immune responses to antigenic proteins depending on their intracellular processing and localisation. Note that most individual protein species are likely to follow only one of the four pathways shown. (B) Modulation of the pattern of immune responses predicted from the use of the sig peptides fused to antigens of interest. In the example used, the ORF2.1 antigen of HEV is the target antigen and contains both linear and conformational B-cell epitopes as well as being likely to contain T-cell epitopes, and the vaccines are plasmid-based DNA vaccines encoding ORF2.1, sig1-2.1 or sig3-2.1, or ubiquitin-2.1 to yield a rapidly degraded product (references 8 and 9). The predicted immune response pathways are shown for animals receiving the different vaccines. Note that the heterogeneous localisation and processing of the sig3-2.1 is unique in activating both the humoral (antibody) and cellular immune responses, with the added potential for positive feedback between the two arms of the immune response.

The activity of the sig1, sig2 and sig3 peptides will be demonstrated by inoculation of Balb/C mice with each of the plasmid constructs ORF2.1, sig1-2.1, sig2-2.1 and sig3-2.1, and GST, sig1-GST, sig2-GST and sig3-GST by standard methods such as gene gun or intramuscular injection, and the immune response in animals receiving each vaccine will be compared by methods such as specific antibody isotype profile, T-cell proliferative responses, and cytolytic T-cell responses. It is anticipated that the different patterns of intracellular processing observed in cell culture in the examples shown herein will also occur in the cells of mice inoculated with the DNA vaccines, and will give rise to modulated immune responses depending on the protein processing of individual constructs. This can be further tested by fusion of each sig peptide to other antigens of interest, including but not limited to the nucleoprotein (NP) and Haemagglutinin (HA) of influenza virus, the envelope and core proteins of Hepatitis C Virus and Hepatitis B Virus, the envelope and gag proteins of the Human Immunodeficiency Virus, and antigens of interest derived from other viral, bacterial, fungal and parasitic pathogens of man and animals as well as cancer-associated antigens. The different immune responses expected from each of the vaccine constructs is shown diagrammatically in FIG. 5.

In conclusion, when encoded by nucleic acid vaccines, the sig1, sig2 and sig3 and related peptides derived from HEV PORF2 will have utility in modulating and enhancing the immune response to fusion protein antigens by virtue of heterogeneous patterns of intracellular processing and localisation, compared to antigens alone or with peptide-antigen fusion proteins (such as ubiquitin-antigen fusion proteins) with homogeneous patterns of intracellular processing and localisation.

EXAMPLE 6

Immune Responses to HEV Signal Peptides Fused to Heterologous Proteins

ORF2.1 series of plasmid constructs were administered to rats via IM injection of 100 μg DNA in saline at 0, 4 and 8 weeks, and antibody responses were measured using the ORF2.1 ELISA (Anderson et al, 1999) (Table 1, FIG. 6, FIG. 7). Plasmids encoding ORF2.1 alone or fused with ubiquitin-A76 failed to elicit any detectable antibodies, whereas Sig1-ORF2.1 induced a strong antibody response in 2/2 rats. Of most interest, Sig3-ORF2.1 induced a strong antibody response in 1/2 rats. Further, most of the protein (the translocated fraction) was degraded within 4 h, which is likely to favour presentation by the MHC-I pathway and induction of CTL response.

The antibody response in rats was also examined by Western immunoblotting against different fragments of ORF2 protein (Li et al, 1997; Riddell et al, 2000), which can reveal reactivity to linear and conformational epitopes (FIG. 7). Notably, both Sig1- and Sig 3-ORF2.1 induced antibodies against the conformational ORF2.1 epitope of HEV (Riddel et al, 2000), a property which we consider to be important for broad efficacy of DNA vaccines. It should also be noted that SIG3-ORF2.1 induced higher levels of antibody reactivity in Western immunoblotting than did SIG1-ORF2.1, probably because of the mixture of intact (conformational) and degraded (linear) antigen which was presented to B cells.

These experiments therefore demonstrate that Sig1 and Sig3 fusions promote enhanced antibody responses compared to unmodified proteins encoded by DNA vaccines, and coupled with the rapid degradation of a proportion of the fusion proteins with Sig3 this would lead to a balance of both CTL responses and antibody responses, which would in turn improve the effectiveness of DNA vaccines encoding antigens such as for example, those of infectious agents or tumours.

EXAMPLE 7

Broad Application of the HEV Signal Peptide Targetting System

DNA vaccine constructs will be prepared in pCI-neo to encode fusions of Sig1 and Sig3 with the following antigens: (i) HCV Core/E1/E2; (ii) HCV Core; (iii) HCV E1/E2; (iv) hepatitis B surface antigen (HBsAg); (v) Influenza nucleoprotein (NP); (vi) Influenza haemagglutinin (HA). Coding sequences for each protein will be amplified from existing plasmids by PCR, and in each case plasmids expressing the corresponding full-length (native) protein and full-length protein fused at the C-terminus of ubiquitin-A76 (control, MHC-I targeting) will also be constructed. Cos cells will be transfected with each plasmid, and the fate of target proteins analysed by pulse-chase radiolabelling, cell fractionation, western immunoblotting and immunoprecipitation to demonstrate whether the targeting effects of HEV Sig1 and Sig3 can be conferred on a very diverse range of target antigens.

Groups of 6 mice each will be immunised at 0 and 4 weeks via IM injection of 100 μg vector (pCI-neo plasmid, negative control), or vector encoding one of the target antigens GST, ORF2.1, HBsAg, NP and HA in the form of (a) full-length protein (control); (b) Ub-A76-protein (control); (c) Sig1-protein; (d) Sig3-protein. The corresponding protein vaccines will serve as additional controls.

Blood will be collected at 0, 4, 8 and 12 weeks and tissues (lymph nodes, spleen) harvested at 12 weeks. Total and isotype-specific IgG responses will be determined by ELISA, giving an indication of the magnitude of the humoral immune response and a surrogate marker for Th1/Th2 bias of the response, respectively. For HA and NP, the analysis will include (a) CTL activity and (b) ELISPOT and/or intracellular cytokine staining to determine the frequency and Th1/Th2 bias of specific T-cells.

To provide a more stringent test of the efficacy provided by HEV Sig1 or Sig3, the HA and NP DNA vaccine constructs will be examined using the model of sublethal influenza infection in mice. Animals will be immunised as before, and at 12 wk all animals will be challenged via intranasal inoculation with a sublethal dose of a mild strain of influenza virus. Five days later, mice are euthanised and lung tissue is harvested for measurement of virus load by plaque assay. These studies will confirm that mixed targeting by HEV Sig sequences will lead to enhanced immune responses.

TABLE 2

Summary of intracellular processing and immunogenicity of HEV signal peptide fusion proteins encoded on DNA plasmids

| Construct | ER translocation | Rapid degradation[a] | Secretion | Antibody induction[b] |
|---|---|---|---|---|
| ORF2.1 | – | + | – | – |
| Sig1-ORF2.1 | ++ | – | – | ++++ |
| Sig2-ORF2.1 | + | + | – | nt |
| Sig3-ORF2.1 | + | + | – | ++ |
| UbA76-ORF2.1 | – | + | – | – |
| GST | – | – | – | nt |
| Sig1-GST | + | – | + | nt |
| Sig2-GST | + | + | + | nt |
| Sig3-GST | + | + | + | nt |
| UbA76-GST | – | + | nt | nt |

[a]Degradation of more than 75% of target protein after 4 hr (ie $t_{1/2}$ <2 hr). For Sig2- and Sig3- proteins only the translocated fraction is degraded.
[b]100 μg DNA IM at 0, 4 and 8 wk, 2 rats per group, ORF2.1-specific Ab measured at 12 wk.

BIBLIOGRAPHY

1. Anderson, D., et al. (1999) *J. Virological Methods* 81:131-142
2. Gurunathan, S. et. al. (2000) *Ann Rev Immunol.* 18:927-74.
3. Forns, X., S. U. et. al. (1999). *Vaccine.* 17: 1992-2002.
4. von Heijne G. et al (1989) *Protein Eng.,* 2:531
5. Khromykh, A. A., et al. (1997). *J Virol.* 71:1497-505.
6. Li, F., et al. (1997) *J. Virological Methods* 52: 289-300
7. Riddell, M., et al. (2000) *J Virol.* 74: 8011-8017
8. Rodriguez F., et. al. (1997). *J Virol.* 71: 8497-503.
9. Rodriguez, F., et. al. (1998) *J Virol.* 72: 5174-81.
10. Torresi, J., F. et. al. (1999). *J Gen Virol.* 80: 1185-8.
11. Varnavski, A. N. et al. (1999) *Virology.* 255:366-75.
12. Varnavski, A. N. et al. (2000). *J Virol.* 74:4394-403.
13. Wolff, J. A. et. al. (1990) *Science.* 247:1465-8.

All publications, patents, and patent applications are incorporated by reference herein, as though individually incorporated by reference.

The invention claimed is:

1. A method for enhancing, in an animal, an immune response to an antigenic polypeptide of interest, said method comprising administering to said animal an effective amount of a composition comprising a nucleic acid construct encoding a fusion protein comprising a processing component and said antigenic polypeptide of interest wherein said processing component provides heterogeneous intracellular localisation to the membrane and cytosol compartments of the antigenic polypeptide when the nucleic acid construct is expressed in a host cell and a resulting enhancement of the immune response to the antigenic polypeptide, wherein said processing component is derived from N-terminal amino acids 1 to 100 of PORF2 protein of Hepatitis E Virus and comprises a sequence of 5 to 100 contiguous amino acids selected from said N-terminal amino acids 1 to 100.

2. A method according to claim 1 wherein said nucleic acid construct encoding a processing component encodes a processing component comprising the sequence of amino acids as set forth in SEQ ID NO: 2 or SEQ ID NO: 3.

3. A method according to claim 1 wherein said processing component comprises the amino acid sequence as set forth in SEQ ID NO: 2 or SEQ ID NO: 3.

4. A method according to claim 1 wherein said processing component comprises the amino acid sequence encoded by a sequence of nucleotides as set forth in SEQ ID NO: 5 or SEQ ID NO: 6.

5. A method for enhancing, in an animal, an immune response to a viral polypeptide, said method comprising administering to said animal an effective amount of a composition comprising a nucleic acid construct encoding a fusion protein comprising a processing component and said viral polypeptide wherein said processing component is encoded by the sequence of nucleotides as set forth in SEQ ID NO: 5 or SEQ ID NO: 6.

6. A method according to claim 4 or 5 wherein said processing component is encoded by the sequence of nucleotides as set forth in SEQ ID NO: 6.

* * * * *